(12) United States Patent
Abuelyaman et al.

(10) Patent No.: US 9,012,531 B2
(45) Date of Patent: *Apr. 21, 2015

(54) DENTAL COMPOSITIONS COMPRISING MIXTURE OF ISOCYANURATE MONOMER AND TRICYCLODECANE MONOMER

(75) Inventors: Ahmed S. Abuelyaman, Woodbury, MN (US); Adrian S. Eckert, Herrsching (DE); Sumita B. Mitra, West St. Paul, MN (US); Timothy D. Dunbar, Woodbury, MN (US); Bradley D. Craig, Lake Elmo, MN (US); Chuntao Cao, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/995,858

(22) PCT Filed: Feb. 6, 2012

(86) PCT No.: PCT/US2012/023911
§ 371 (c)(1),
(2), (4) Date: Jun. 19, 2013

(87) PCT Pub. No.: WO2012/112321
PCT Pub. Date: Aug. 23, 2012

(65) Prior Publication Data
US 2014/0220512 A1     Aug. 7, 2014

Related U.S. Application Data

(60) Provisional application No. 61/433,018, filed on Feb. 15, 2011.

(51) Int. Cl.
*A61K 6/083* (2006.01)
*A61K 6/09* (2006.01)
*A61K 6/00* (2006.01)

(52) U.S. Cl.
CPC ............ *A61K 6/083* (2013.01); *A61K 6/0073* (2013.01); *A61K 6/0008* (2013.01); *A61K 6/0005* (2013.01); *A61K 6/09* (2013.01); *A61K 6/0061* (2013.01)

(58) Field of Classification Search
CPC .... A61K 6/083; A61K 6/0008; A61K 6/0073
USPC ........................................................ 523/115
See application file for complete search history.

(56) References Cited

U.S. PATENT DOCUMENTS 3,347,954 A    10/1967   Bredereck
3,541,068 A    11/1970   Taylor
(Continued)

FOREIGN PATENT DOCUMENTS

EP    0209365    1/1987
EP    0319829    6/1989
(Continued)

OTHER PUBLICATIONS

International Search Report PCT/US2012/023911; Sep. 16, 2012; 4 pgs.
(Continued)

*Primary Examiner* — Michael Pepitone
(74) *Attorney, Agent, or Firm* — Carolyn A. Fischer

(57) ABSTRACT

Hardenable compositions are described comprising at least one multifunctional ethylenically unsaturated isocyanurate monomer and at least one multifunctional ethylenically unsaturated tricyclodecane monomer. In favored embodiments, the compositions further comprise filler and are suitable dental restorations.

23 Claims, 1 Drawing Sheet

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A | 4/1974 | Smith | |
| 3,825,518 A | 7/1974 | Foster | |
| 4,071,424 A | 1/1978 | Dart | |
| 4,250,053 A | 2/1981 | Smith | |
| 4,394,403 A | 7/1983 | Smith | |
| 4,503,169 A | 3/1985 | Randklev | |
| 4,544,742 A | 10/1985 | Schmitt | |
| 4,642,126 A | 2/1987 | Zador | |
| 4,648,843 A | 3/1987 | Mitra | |
| 4,652,274 A | 3/1987 | Boettcher | |
| 4,737,593 A | 4/1988 | Ellrich | |
| 4,744,827 A | 5/1988 | Winkel | |
| 4,762,863 A | 8/1988 | Sasaki | |
| 4,772,530 A | 9/1988 | Gottschalk | |
| 4,874,450 A | 10/1989 | Gottschalk | |
| 4,886,861 A | 12/1989 | Janowicz | |
| 4,954,414 A | 9/1990 | Adair | |
| 5,055,372 A | 10/1991 | Shanklin | |
| 5,057,393 A | 10/1991 | Shanklin | |
| 5,130,347 A | 7/1992 | Mitra | |
| 5,154,762 A | 10/1992 | Mitra | |
| 5,302,630 A | 4/1994 | Mukai | |
| 5,324,879 A | 6/1994 | Hawthorne | |
| 5,332,429 A | 7/1994 | Mitra | |
| 5,501,727 A | 3/1996 | Wang | |
| 5,545,676 A | 8/1996 | Palazzotto | |
| 5,624,260 A | 4/1997 | Wilcox | |
| 5,865,803 A | 2/1999 | Major | |
| 5,893,714 A | 4/1999 | Arnold | |
| 5,918,772 A | 7/1999 | Keller | |
| 5,944,419 A | 8/1999 | Streiff | |
| 5,962,550 A | 10/1999 | Akahane | |
| 6,126,922 A | 10/2000 | Rozzi | |
| 6,184,339 B1 | 2/2001 | Stansbury | |
| 6,284,898 B1 | 9/2001 | Moszner | |
| 6,387,981 B1 | 5/2002 | Zhang | |
| 6,572,693 B1 | 6/2003 | Wu | |
| 6,617,413 B1 | 9/2003 | Bruchmann | |
| 6,670,436 B2 | 12/2003 | Burgath | |
| 6,730,156 B1 | 5/2004 | Windisch | |
| 6,794,520 B1 | 9/2004 | Moszner | |
| 6,899,948 B2 | 5/2005 | Zhang | |
| 7,090,721 B2 | 8/2006 | Craig | |
| 7,090,722 B2 | 8/2006 | Budd | |
| 7,156,911 B2 | 1/2007 | Kangas | |
| 7,241,437 B2 | 7/2007 | Davidson | |
| 7,374,863 B2 | 5/2008 | Sugasaki | |
| 7,601,767 B2 | 10/2009 | Ruppert | |
| 7,649,029 B2 | 1/2010 | Kolb | |
| 7,674,850 B2 | 3/2010 | Karim | |
| 7,794,917 B2 | 9/2010 | Mori | |
| 8,329,776 B2 | 12/2012 | Hecht | |
| 8,426,490 B2 | 4/2013 | Bissinger | |
| 8,710,113 B2 * | 4/2014 | Eckert et al. | 522/175 |
| 2003/0008967 A1 | 1/2003 | Hecht | |
| 2003/0187091 A1 | 10/2003 | Moszner | |
| 2003/0215750 A1 | 11/2003 | Inno | |
| 2005/0171231 A1 * | 8/2005 | Diggins | 523/105 |
| 2006/0187752 A1 | 8/2006 | Keller | |
| 2006/0216646 A1 | 9/2006 | Goto | |
| 2007/0090079 A1 | 4/2007 | Kelller | |
| 2007/0100020 A1 * | 5/2007 | Nakatsuka et al. | 523/118 |
| 2007/0172789 A1 | 7/2007 | Muller | |
| 2007/0231745 A1 | 10/2007 | Oohashi | |
| 2008/0076848 A1 | 3/2008 | Jin | |
| 2008/0167399 A1 | 7/2008 | Utterodt | |
| 2008/0194722 A1 | 8/2008 | Abuelyaman | |
| 2008/0311488 A1 | 12/2008 | Su | |
| 2009/0032989 A1 | 2/2009 | Karim | |
| 2009/0036565 A1 | 2/2009 | Utterodt | |
| 2009/0111904 A1 | 4/2009 | Odaka | |
| 2010/0087611 A1 | 4/2010 | Urakawa | |
| 2010/0160557 A1 * | 6/2010 | Murofushi et al. | 525/55 |
| 2013/0012614 A1 | 1/2013 | Abuelyaman | |

FOREIGN PATENT DOCUMENTS

| | | |
|---|---|---|
| EP | 1340472 | 9/2003 |
| EP | 2008636 | 12/2008 |
| EP | 2180354 | 4/2010 |
| EP | 2272486 | 1/2011 |
| JP | 60-123478 | 7/1985 |
| JP | 08-034707 | 2/1996 |
| JP | 9316111 | 12/1997 |
| JP | 2001-39956 | 2/2001 |
| JP | 2005-179282 | 7/2005 |
| JP | 2009-74027 | 4/2009 |
| JP | 2009-108216 | 5/2009 |
| WO | WO 01/30305 | 5/2001 |
| WO | WO 01/30307 | 5/2001 |
| WO | WO 03/063804 | 8/2003 |
| WO | WO 2005/014721 | 2/2005 |
| WO | WO 2006/122081 | 11/2006 |
| WO | WO 2008/082881 | 7/2008 |
| WO | WO 2008146685 A1 * | 12/2008 |
| WO | WO 2009/091551 | 7/2009 |
| WO | WO 2009/151957 | 12/2009 |
| WO | WO 2012/003136 | 1/2012 |
| WO | WO 2012/106083 | 8/2012 |
| WO | WO 2012/112321 | 8/2012 |
| WO | WO 2012/112350 | 8/2012 |

OTHER PUBLICATIONS

Surface & Colloid Science, vol. 6, Matijevic, E., Wiley Interscience, 1973.

Watts et al, "Determination of Polymerization Shrinkage Kinetics in Visible Light Cured Materials: Methods of Development", Dental Materials, Oct. 1991, pp. 281-286.

Mahmoodian et al., "Synthesis of organic-inorganic hybrid compounds based on Bis-GMA and its sol-gel behavior analysis using Taguchi method", Dental Materials 24 (2008) 514-521.

Enikolopyan et al., "Catalyzed Chain Transfer to Monomer in Free Radical Polymerization"; *J. Polym. Sci., Polym. Chem.* 1981, 19, 879-889.

Moad et al, "Chain Transfer Activity of ω-Unsaturated Methyl Methacrylate Oligomers"; *Macromolecules*, 1996, 29, 7717-7726.

Hutson et al, "Chain Transfer Activity of ω-Unsaturated Methacrylic Oligomers in Polymerizations of Methacrylic Monomers", *Macromolecules*, 2004, 37, 4441-4452.

R. R. Cara et al, "Influence of Bis-GMA Derivative Monomer-Based Particulate Composite Resins on the Cuspal Deformation and Microleakage of Restored Teeth", Particulate Science and Technology 28; 191-206 (2010).

Sakaguchi et al.; "Analysis of Strain Gage Method for Measurement of Post-Gel Shrinkage in Resin Composites", Dent Mater. Jul. 1997, 13, 233-239.

Mitra, "Dental Composites Prepared from Resin Matrices Containing Ethylenically Unsaturated Carbamoyl Isocyanurates", Polymer Preprints, Division of Polymer Chemistry, American Chemical Society, vol. 38, No. 2, pp. 103-104. XP008085102.

* cited by examiner

DENTAL COMPOSITIONS COMPRISING MIXTURE OF ISOCYANURATE MONOMER AND TRICYCLODECANE MONOMER

BACKGROUND

Various ethylenically unsaturated monomers, such as (meth)acrylate monomers have been employed in hardenable dental compositions.

Certain dental materials comprising isocyanurate monomer have been described for example in U.S. Pat. No. 4,648,843; U.S. Pat. No. 5,302,630; U.S. Pat. No. 6,617,413; EP 2 008 636; and US2009/0032989.

Further, certain dental materials comprising tricyclodecane monomers have been described in US 2009/0036565; US 2008/0167399; U.S. Pat. No. 7,601,767; and U.S. Pat. No. 4,744,827.

SUMMARY

A hardenable composition is described comprising at least one multifunctional ethylenically unsaturated isocyanurate monomer and at least one multifunctional ethylenically unsaturated tricyclodecane monomer. The hardenable composition is suitable for use in a dental (e.g. restorative) composition. The composition can exhibit a variety of beneficial properties such as low volume shrinkage and/or low stress deflection.

Also described are dental articles and methods of treating a tooth surface.

DETAILED DESCRIPTION

Figure 1:
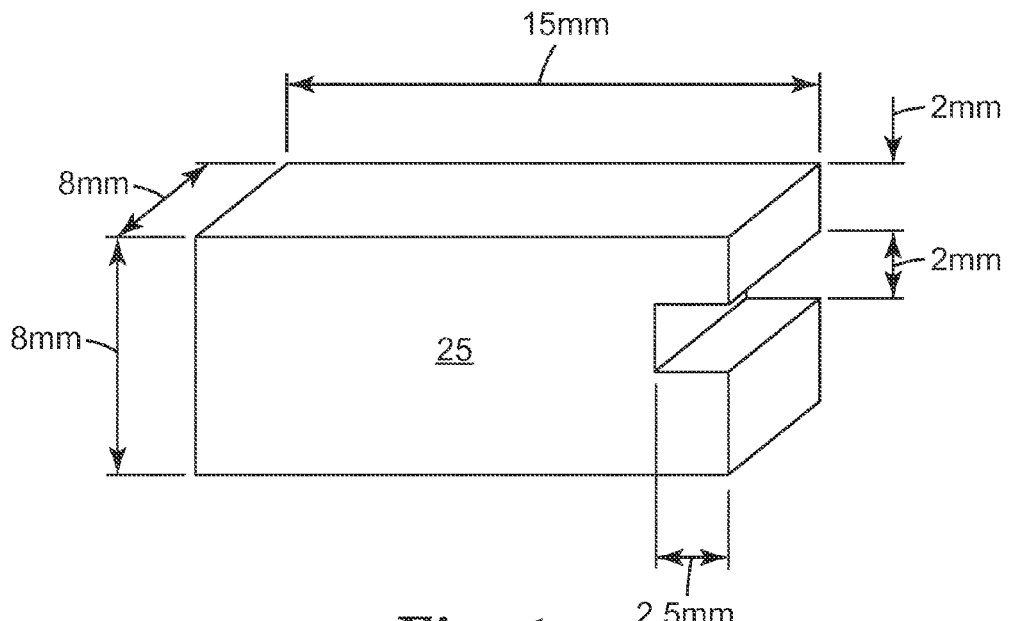
FIG. 1 depicts a machined aluminum block utilized as a sample holder for a curable composition during Stress Deflection testing.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein, "dental article" refers to an article that can be adhered (e.g., bonded) to a tooth structure or dental implant. Dental articles include, for example, crowns, bridges, veneers, inlays, onlays, fillings, orthodontic appliances and devices.

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

As used herein, an "oral surface" refers to a soft or hard surface in the oral environment. Hard surfaces typically include tooth structure including, for example, natural and artificial tooth surfaces, bone, and the like.

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, "hardener" refers to something that initiates hardening of a resin. A hardener may include, for example, a polymerization initiator system, a photoinitiator system, a thermal initiator and/or a redox initiator system.

As used herein, the term "(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The hardenable (e.g. dental) compositions described herein comprise at least one multifunctional ethylenically unsaturated isocyanurate monomer and at least one multifunctional ethylenically unsaturated tricyclodecane monomer. The phrase "multifunctional ethylenically unsaturated" means that the monomers each comprise at least two ethylenically unsaturated (e.g. free radically) polymerizable groups, such as (meth)acrylate groups.

The ethylenically unsaturated (e.g. free radically) polymerizable groups are generally bonded to the core or backbone unit via a (e.g. divalent) linking group The linking group(s) terminate with the ethylenically unsaturated polymerizable group. Thus, the ethylenic unsaturation is present in a terminal group, rather than within the backbone of the monomer. In favored embodiment, such ethylenically unsaturated group is a free radically polymerizable group including (meth)acryl such as (meth)acrylamide ($H_2C$=CHCON— and $H_2C$=CH($CH_3$)CON—) and (meth) acrylate ($CH_2$CHCOO— and $CH_2$C($CH_3$)COO—). Other ethylenically unsaturated polymerizable groups include vinyl ($H_2C$=C—) including vinyl ethers ($H_2C$=CHOCH—). The ethylenically unsaturated terminal polymerizable group(s) is preferably a (meth)acrylate group, particularly for compositions that are hardened by exposure to actinic (e.g. UV) radiation. Further, methacrylate functionality is typically preferred over the acrylate functionality in curable dental compositions.

The isocyanurate monomer generally comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group.

The trivalent isocyanurate core structure generally has the formula:

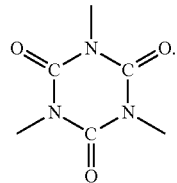

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate monomers comprising urethane linkages for providing improved properties such as reduced shrinkage, and/or increased mechanical properties, e.g., diametral tensile strength (DTS). Thus, in some embodiments, the divalent linking groups of the iscosyanurate monomer are free of urethane linkages. In some favored embodiments, the divalent linking group comprises an ester linkage such as an aliphatic or aromatic diester linkage.

The isocyanurate monomer typically has the general structure

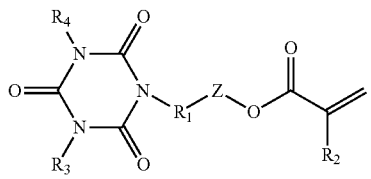

wherein $R_1$ is a straight chain, branched or cyclic alkylene, arylene, or alkarylene, optionally including a heteroatom (e.g. oxygen, nitrogen, or sulfur); $R_2$ is hydrogen or methyl; Z is alkylene, arylene, or alkarylene linking group comprising at least one moiety selected from urethane, ester, thioester, ether, or thioether, and combinations of such moieties; and at least one of $R_3$ or $R_4$ is

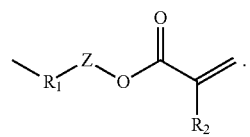

$R_1$ is typically a straight chain, branched or cyclic alkylene, optionally including a heteroatom, having no greater than 12 carbons atoms. In some favored embodiments, $R_1$ has no greater than 8, 6, or 4 carbon atoms. In some favored embodiments, $R_1$ comprises at least one hydroxyl moiety.

In some embodiments, Z comprises an aliphatic or aromatic ester linkage such as a diester linkage.

In some embodiment, Z further comprises one or more ether moieties. Hence, the linking group may comprise a combination of ester or diester moieties and one or more ether moieties.

For embodiments, wherein the isocyanurate monomer is a di(meth)acrylate monomer, $R_3$ or $R_4$ is hydrogen, alkyl, aryl, or alkaryl, optionally including a heteroatom.

$R_1$ is generally derived from the starting (e.g. hydroxy terminated) isocyanurate precursor. Various isocyanurate precursor materials are commercially available from TCI America, Portland, Oreg. The structures of exemplary isocyanurate precursor materials are depicted as follows:

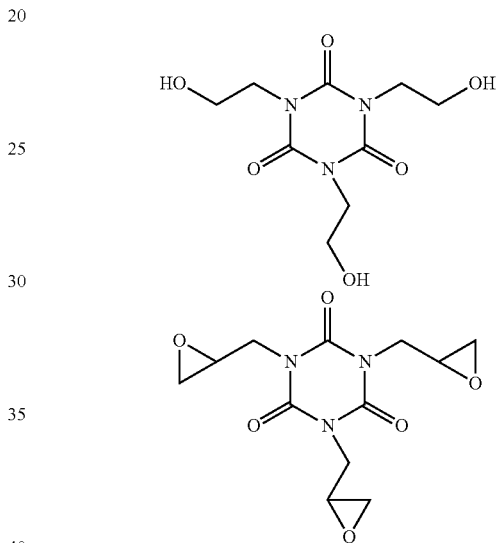

The isocyanurate (meth)acrylate monomers disclosed herein having a linking groups comprising an oxygen atom of an ester moiety were generally prepared by reaction of hydroxy or epoxy terminated isocyanurates with (meth)acrylated carboxylic acids such as mono-(2-methacryloxyethyl) phthalic acid and mono-(2-methacryloxytheyl)succinic acid.

Suitable (meth)acrylated carboxylic acids include for example mono-(2-methacryloxyethyl)phthalic acid(s), mono-(2-methacryloxytheyl)succinic acid, and mono-(2-methacryloxyethyl)maleic acid. Alternatively, the carboxylic acid may comprise (meth)acrylamido functionally such as methacrylamido derivatives of naturally occurring amino acids such as methacrylamidoglycine, methacrylamidoleucine, methacrylamidoalanine etc.

In some embodiments, a single (meth)acrylated carboxylic acid is reacted with a single hydroxyl terminated isocyanurate (e.g. tris-(2-hydroxylethyl)isocyanurate). When a sufficient molar ratio of (meth)acrylate carboxylic acid is utilized such that all the hydroxyl groups of the ring are reacted, such synthesis can produce a single reaction product wherein each of the free radically terminated groups, bonded to the nitrogen atoms of the trivalent isocyanuric acid ring, are the same. However, when a single epoxy terminated isocyanurate is reacted with a single carboxylic acid, the reaction product generally comprises more than one isomer in the reaction product.

When two different hydroxy or epoxy terminated isocyanurates and/or two different (e.g. (meth)acrylated) carboxylic acids are utilized, a statistical mixture of reaction products are obtained based on the relative amounts of reactants. For example, when a mixture of a (meth)acrylated aromatic carboxylic acid and a (meth)acrylate aliphatic carboxylic acid are utilized, some of the free radically terminated divalent linking groups bonded to the nitrogen atom of the trivalent isocyanuric acid ring comprise an aromatic group, whereas others do not. Further, when a combination (e.g. 1 equivalent) of a hydroxyl terminated carboxylic acid and (e.g. 2 equivalents) of a monocarboxylic acid (such as octanoic acid) is reacted with a single hydroxyl terminated isocyanurate (e.g. tris-(2-hydroxylethyl)isocyanurate), a mono(meth)acrylate isocyanurate can be prepared as further described in U.S. Provisional Application No. 61/319,534, filed Mar. 31, 2010. Such mono(meth)acrylate isocyanurate is suitable for use as a reactive diluent.

Alternatively, isocyanurate(meth)acrylate monomers having ether group containing linking groups can be synthesized. For example, in one illustrative synthesis, phthalic acid anhydride can be reacted with a mono-methacrylated di, tri, tetra or polyethylenegylcol in the presence of a catalytic amount of 4-(dimethylamino)pyridine (DMAP) and butylated hydroxytoluene inhibitor (BHT) at 95° C. for a 3-6 hours to form a mono-methaycrylated polyethyleneglycol phthalic acid mono-ester. The obtained methacrylated acid can be reacted, in acetone, with tris-(2-hydroxyethyl)isocyanurate using dicyclohexyl carbodiimide (DCC) at 0-5° C. then at room temperature. Such reaction scheme is depicted as follows:

In another illustrative synthesis, tris(2-hydroxyethyl)isocyanurate can be reacted with ethylene oxide to form a polyethylene glycol terminated with a hydroxyl group. The OH termini can be esterified with meth(acrylic) acid to provide a product where the linking group is a polyether. Such reaction scheme is depicted as follows:

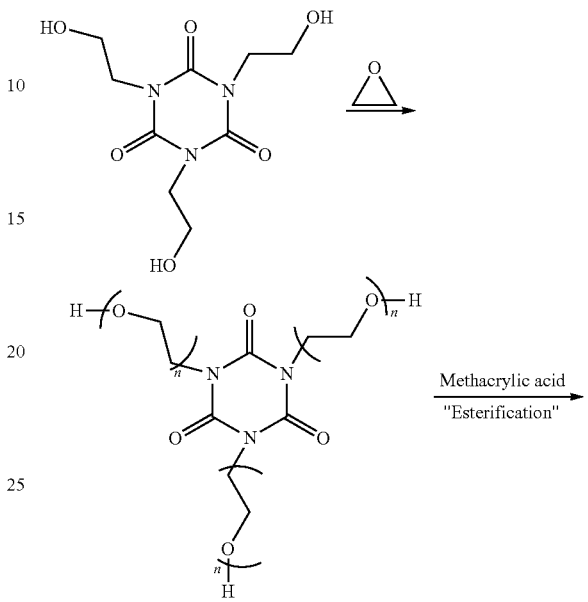

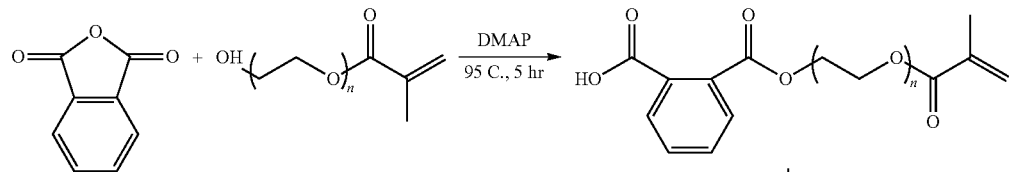

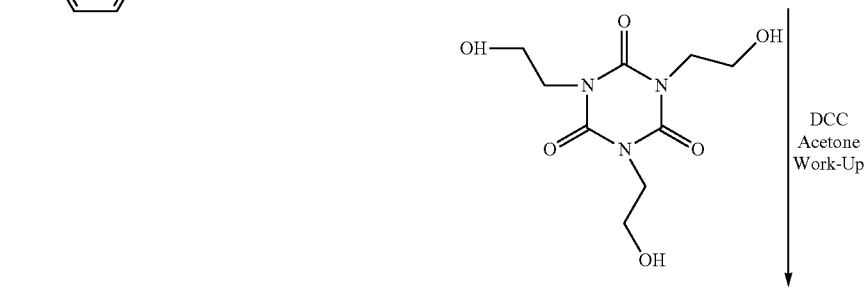

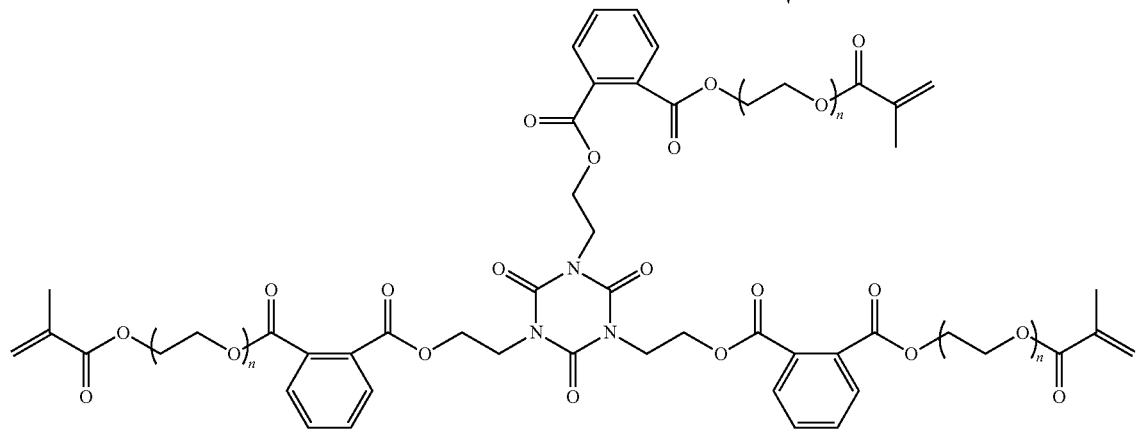

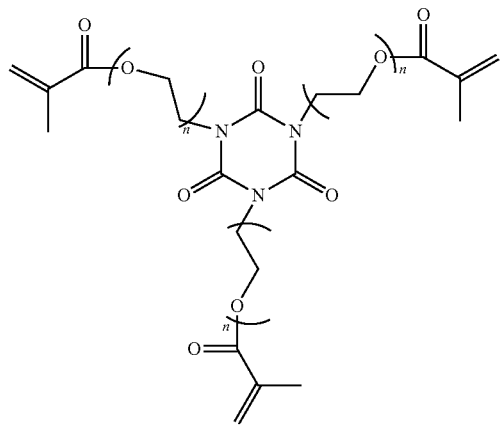

The isocyanurate monomer is preferably a multi (meth)acrylate such as a di(meth)acrylate isocyanurate monomer or a tri(meth)acrylate isocyanurate monomer.

The di(meth)acrylate monomer has the general structure:

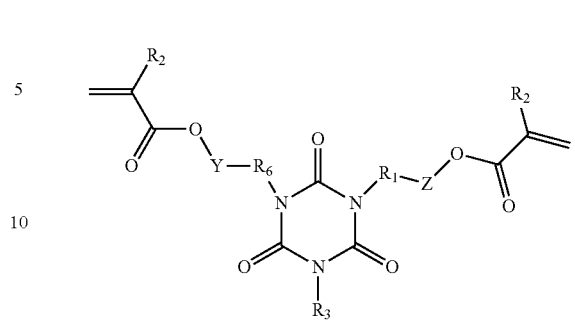

wherein $R_1$, $R_2$, $R_3$ and Z are as previously described; $R_6$ is a straight chain, branched, or cyclic alkylene, arylene, or alkarylene, optionally including a heteroatom (e.g. oxygen, nitrogen, or sulfur); and Y is alkylene, arylene, or alkarylene linking group comprising at least one moiety selected from urethane, ester, thioester, ether, or thioether, and combinations of such moieties.

Illustrative di(meth)acrylate isocyanurate monomers includes:

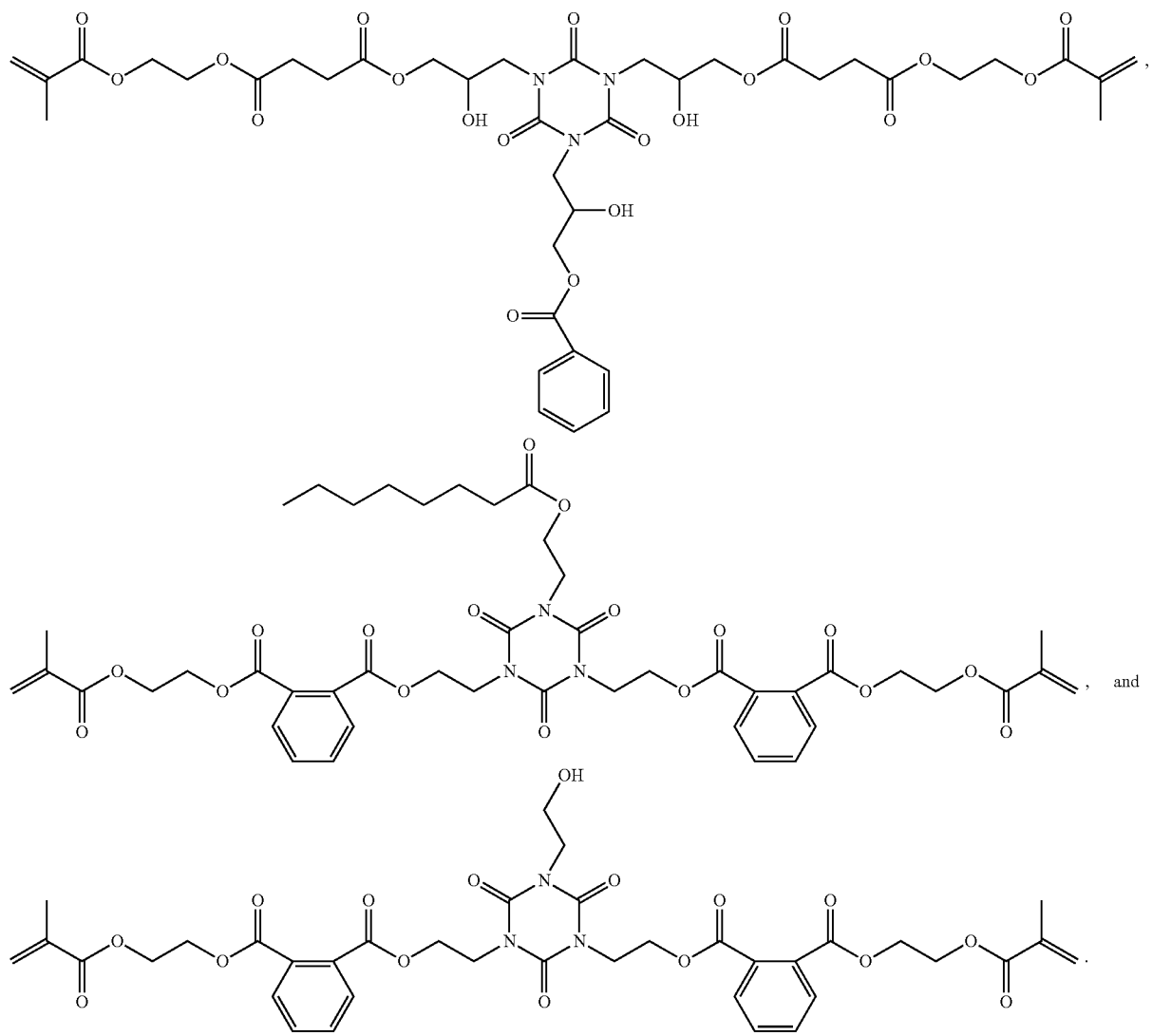

In some favored embodiments, the tri(meth)acrylate monomer has the general structure:

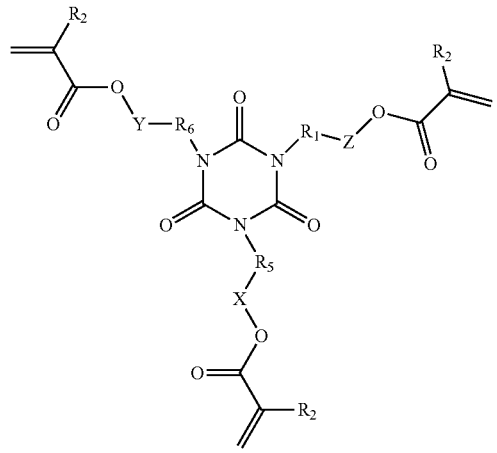

wherein $R_1$, $R_5$, and $R_6$ are independently a straight chain, branched, or cyclic alkylene, arylene, or alkarylene, optionally including a heteroatom (e.g. oxygen, nitrogen, or sulfur); $R_2$ is hydrogen or methyl; X, Y, and Z are independently alkylene, arylene, or alkarylene linking group comprising at least one moiety selected from urethane, ester, thioester, ether, thioether, or combinations of such moieties; and $R_2$ is hydrogen or methyl.

In some embodiments, $R_1$, $R_5$, and $R_6$ comprise at least one hydroxyl moiety.

Illustrative tri(meth)acrylate isocyanurate monomers include for example:

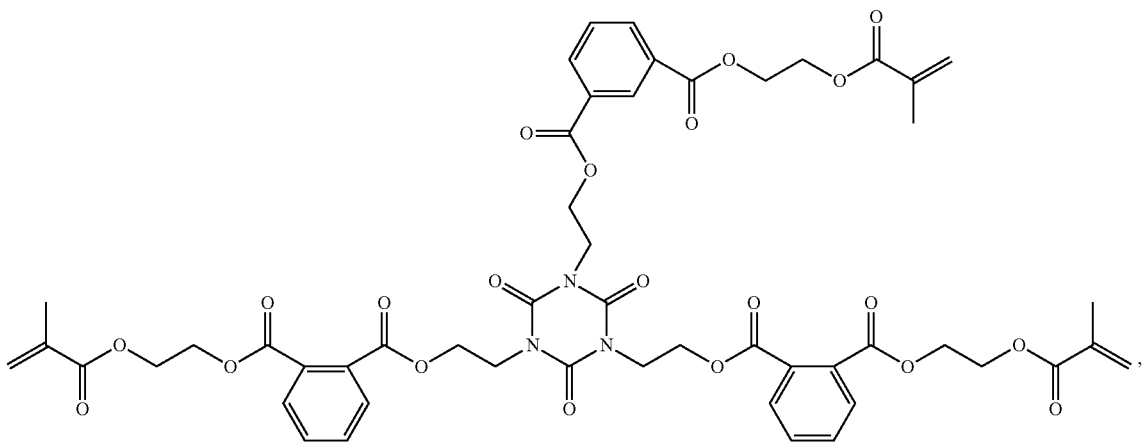

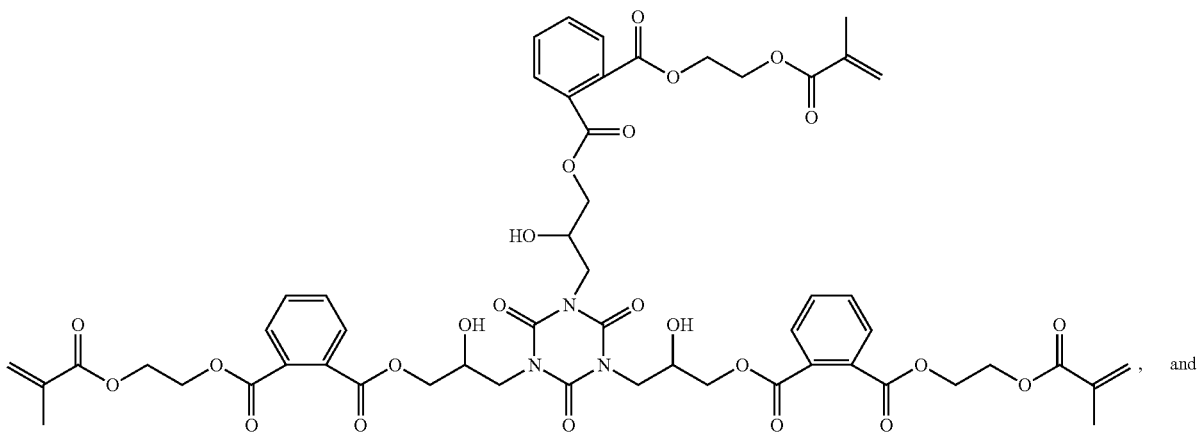

-continued

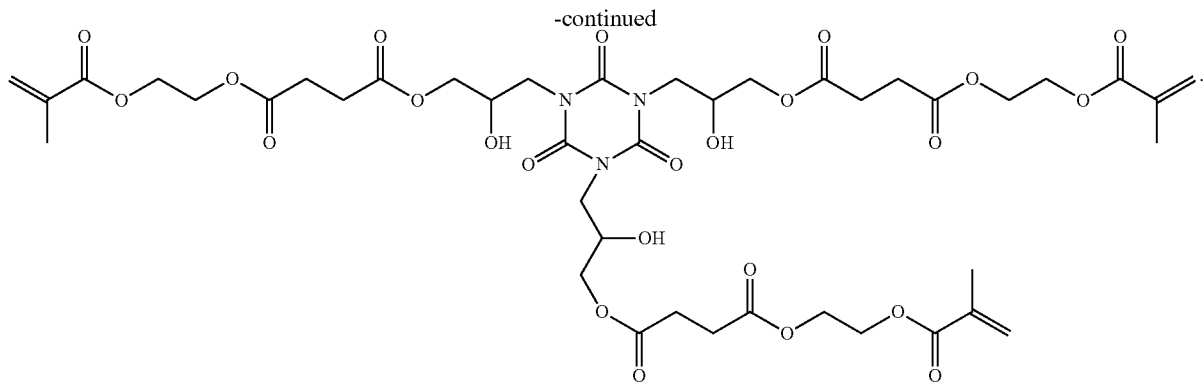

The synthesis of various multifunctional ethylenically unsaturated isocyanurate monomers, such as the species described above, are further described in U.S. Provisional Application No. 61/319,534, filed Mar. 31, 2010; incorporated herein by reference.

The concentration of monomer in the hardenable (i.e. polymerizable) dental composition described herein can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

The polymerizable resin portion of the hardenable (i.e. polymerizable) dental composition described herein comprises at least 10 wt-%, 15 wt-%, 20 wt-%, or 25 wt-%, multifunctional ethylenically unsaturated isocyanurate monomer(s). The isocyanurate monomer may comprise a single monomer or a blend of two or more isocyanurate monomers. The total amount of isocyanurate monomer(s) in the polymerizable resin portion of the hardenable (i.e. polymerizable) dental composition is typically no greater than 90 wt-%, 85 wt-%, 80 wt-%, or 75 wt-%.

In some embodiments, the total amount of isocyanurate monomer(s) in the polymerizable resin portion of the hardenable (i.e. polymerizable) dental composition is at least 30 wt-%, 35 wt-%, or 40 wt-% and no greater than 70 wt-%, 65 wt-%, or 60 wt-%.

The filled hardenable (i.e. polymerizable) dental composition described herein

Typically comprises at least 5 wt-%, 6 wt-%, 7 wt-%, 8 wt-%, or 9 wt-% of multifunctional ethylenically unsaturated isocyanurate monomer(s). The total amount of isocyanurate monomer(s) of the filled hardenable (i.e. polymerizable) dental composition is typically no greater than 20 wt-%, or 19 wt-%, or 18 wt-%, or 17 wt-%, or 16 wt-%, or 15 wt-%.

The hardenable (e.g. dental) composition described herein further comprises at least one multifunctional ethylenically unsaturated tricyclodecane monomer. The tricyclodecane monomer may comprise a single monomer or a blend of two or more tricyclodecane monomers. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

Various multifunctional ethylenically unsaturated tricyclodecane monomers can be utilized in the composition, such as described in EP Application No. 10168240.9, filed Jul. 2, 2010; incorporated herein by reference. Tricyclodecane monomers generally have the core structure (i.e. backbone unit (U):

In some favored embodiments, the tricyclodecane monomers generally have the core structure (i.e. backbone unit (U):

Such tricyclodecane monomers can be prepared for example from starting materials such as

(a + b) = 1 and (c + d) = 1,
Mw = 312.5

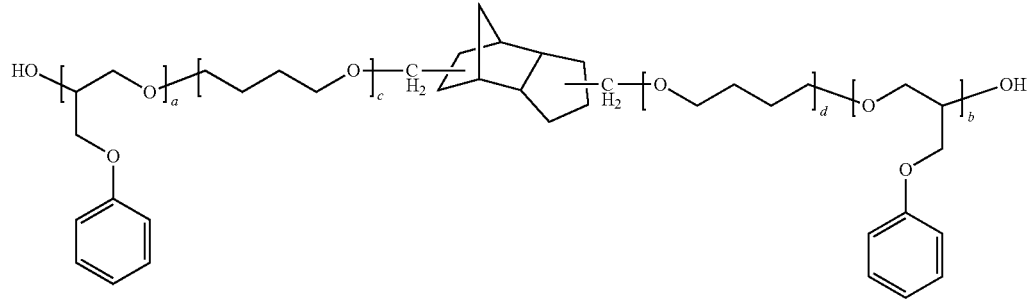

(a + b) = 1 and (c + d) = 1,
Mw = 418.6

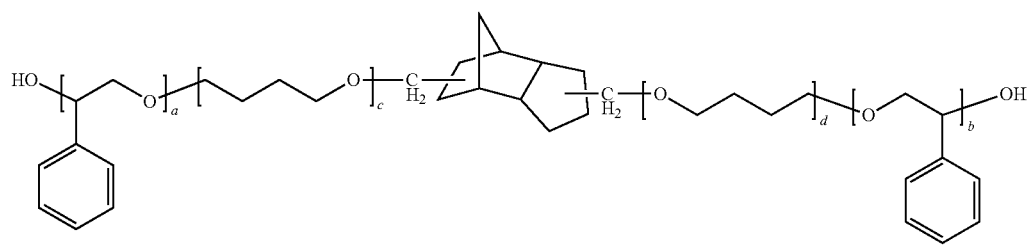

(a + b) = 1 and (c + d) = 1,
Mw = 388.6

The backbone unit (U) typically comprises one or two spacer unit(s) (S) bonded to the backbone unit (U) via an ether linkage. At least one spacer unit (S) comprises a CH(Q)-OG chain, wherein each group G comprises a (meth)acrylate moiety and Q comprises at least one group selected from hydrogen, alkyl, aryl, alkaryl and combinations thereof. In some embodiments, Q is hydrogen, methyl, phenyl, phenoxymethyl, and combinations thereof. G may be bonded to the spacer unit(s) (S) via a urethane moiety.

In some embodiments, the spacer unit(s) (S) typically comprise

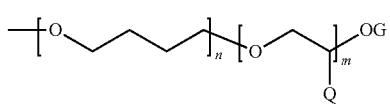

wherein m is 1 to 3; n is 1 to 3; and Q is hydrogen, methyl, phenyl, phenoxymethyl.

In other embodiments, the spacer unit(s) (S) typically comprise

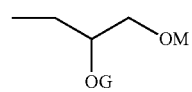

wherein M=phenyl.

In some embodiments, the tricyclodecane monomer may be characterized by the structures

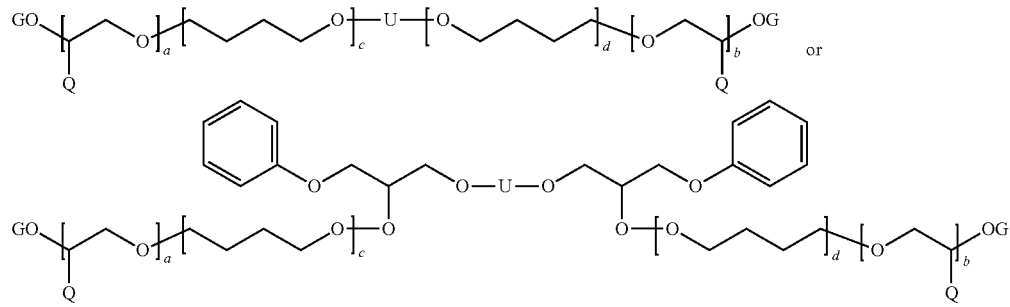

wherein for each of these tricyclodecane monomer structures a, b is 0 to 3; c, d=0 to 3; (a+b) is 1 to 6; (c+d) is 1 to 6; and Q is independently hydrogen, methyl, phenyl or phenoxymethyl.

Some illustrative species of such multifunctional ethylenically unsaturated tricyclodecane monomers are described in the following table.

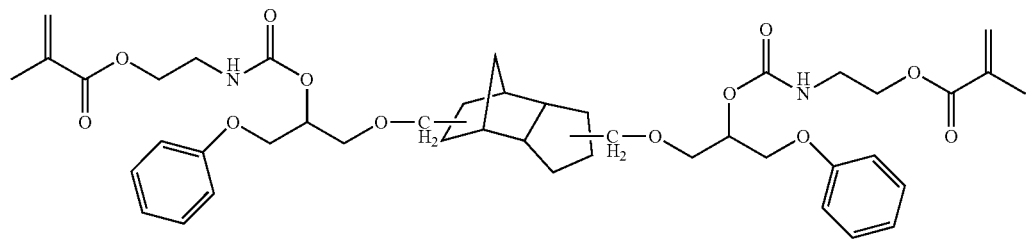
Mw = 807.0; $n_D^{20}$ = 1.531; η = 1400 Pa*S
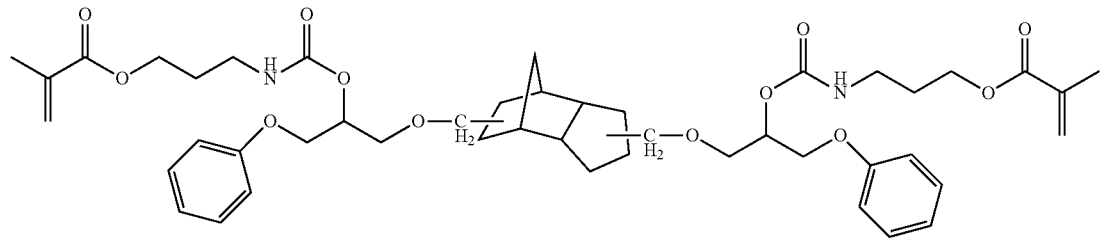
Mw = 835.1
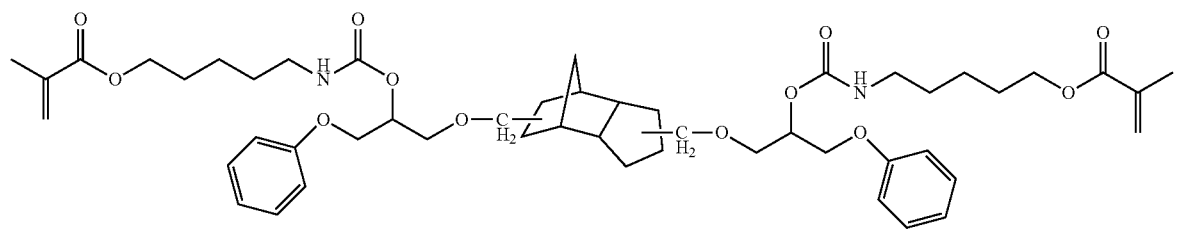
Mw = 891.2
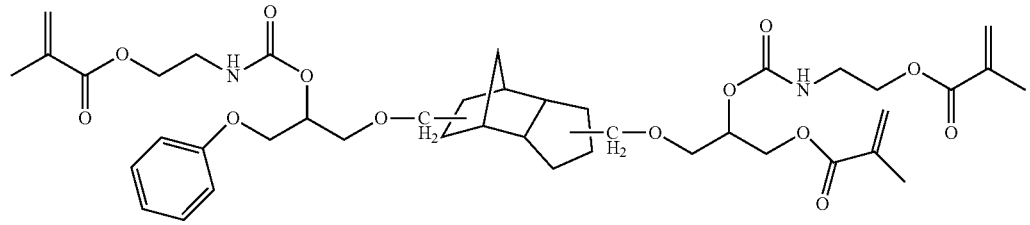
Mw = 798.9
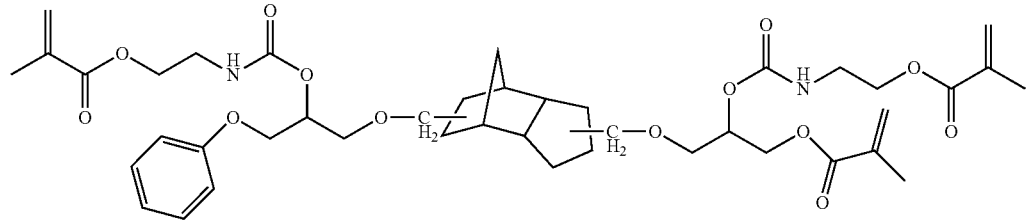
Mw = 798.9
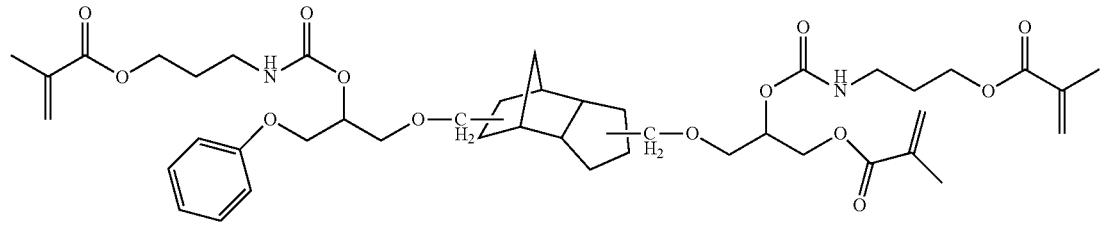
Mw = 827.0

-continued
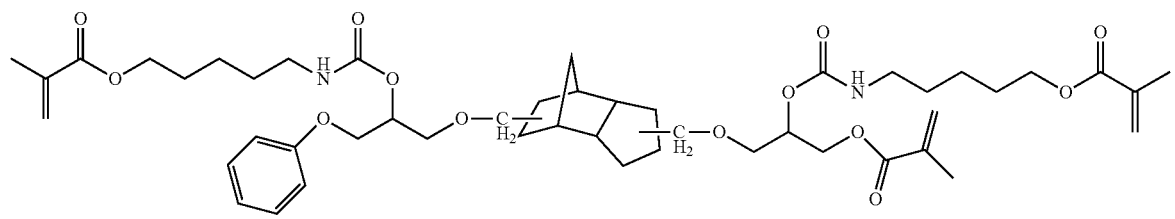
Mw = 883.1
TCD-Alcohol - IEM, reaction product of tricyclo[5.2.1.0²,⁶]decane dimethanole (TCD-Alcohol DM) and IEM
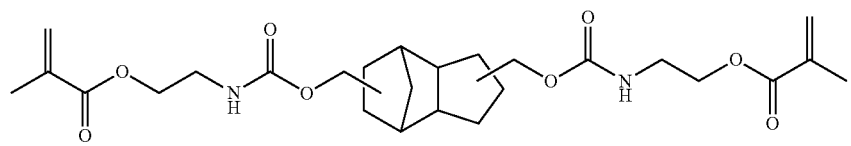
Mw = 506.6; $n_D^{20}$ = 1.510; $\eta$ = 1100 Pa*s
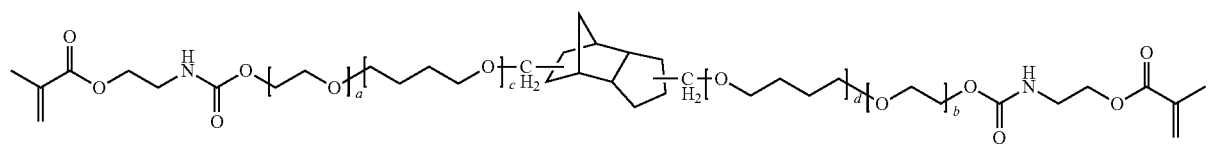
(a + b) = 1 and (c + d) = 1,
Mw = 622.8; $n_D^{20}$ = 1.503; $\eta$ = 45 Pa*s
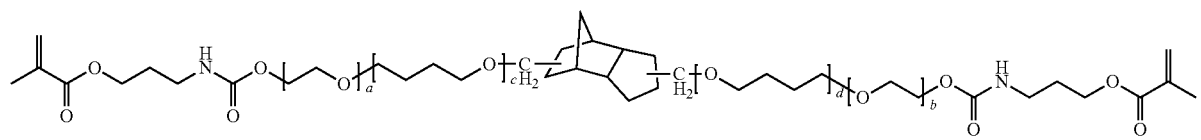
with (a + b) = 1 and (c + d) = 1,
Mw = 650.9
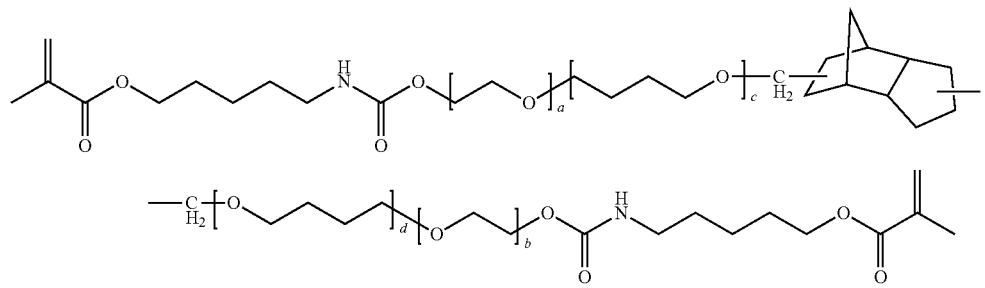
(a + b) = 1 and (c + d) = 1,
Mw = 707.9
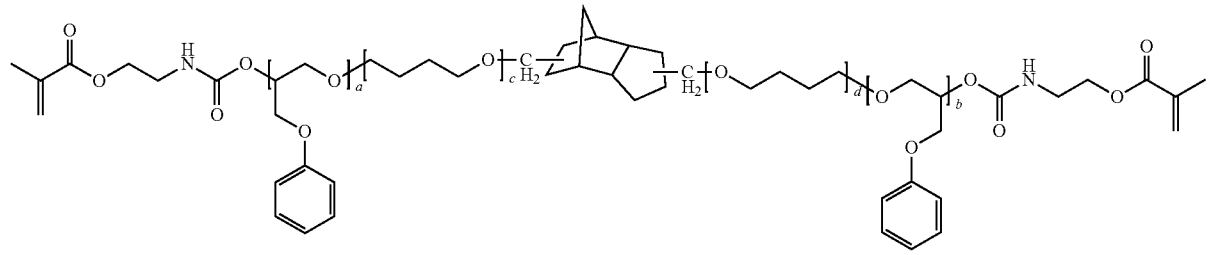
(a + b) = 1 and (c + d) = 1,
Mw = 728.9; $n_D^{20}$ = 1.518; $\eta$ = 433 Pa*s -continued
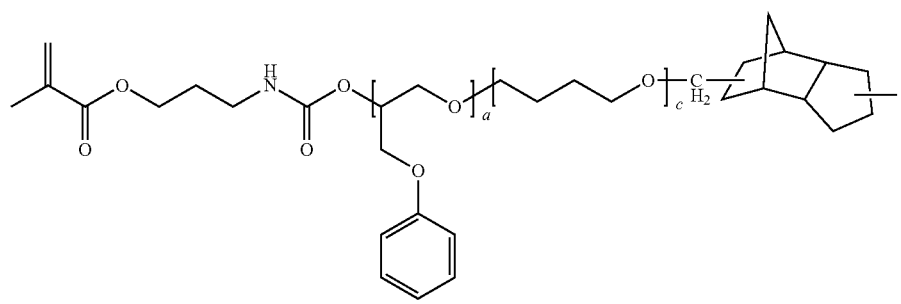
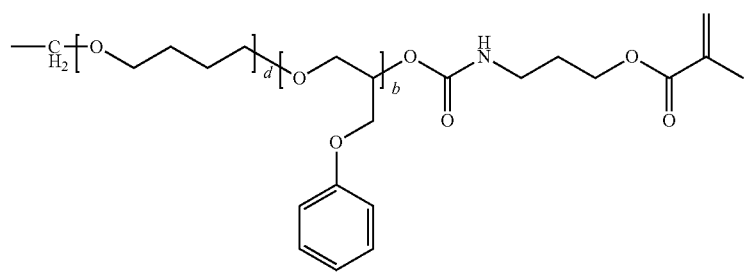
with (a + b) = 1 and (c + d) = 1,
Mw = 757.0
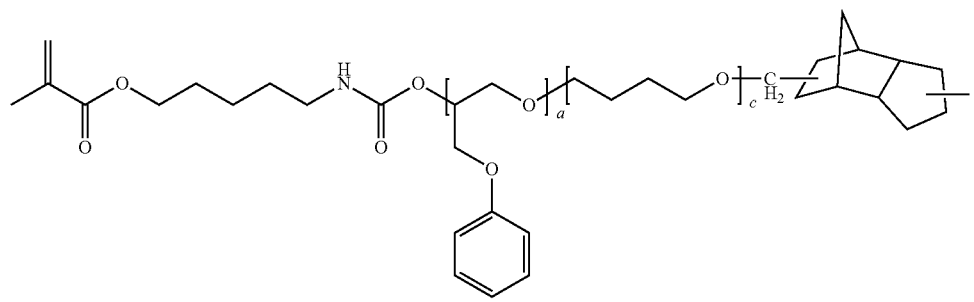
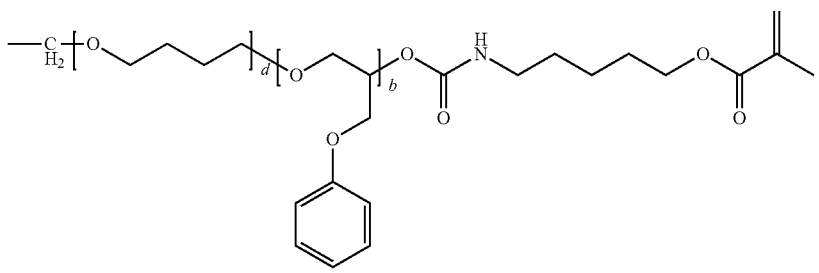
with (a + b) = 1 and (c + d) = 1,
Mw = 813.1; $n_D^{20}$ = 1.513; η = 35 Pa*s
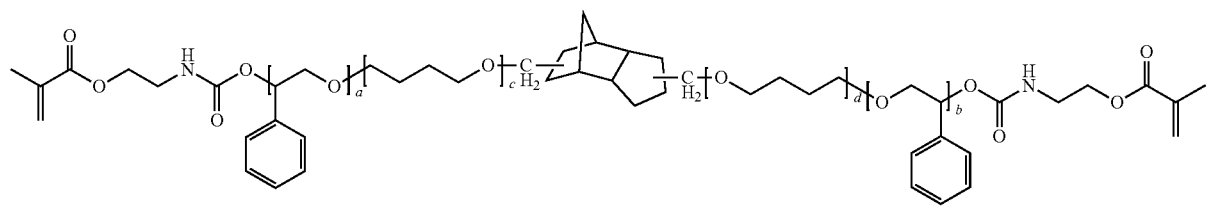
(a + b) = 1 and (c + d) = 1,
Mw = 698.9

-continued

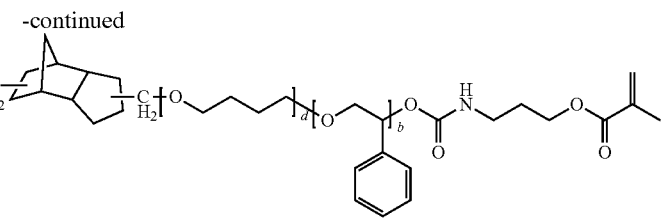

with (a + b) = 1 and (c + d) = 1,
Mw = 727.0

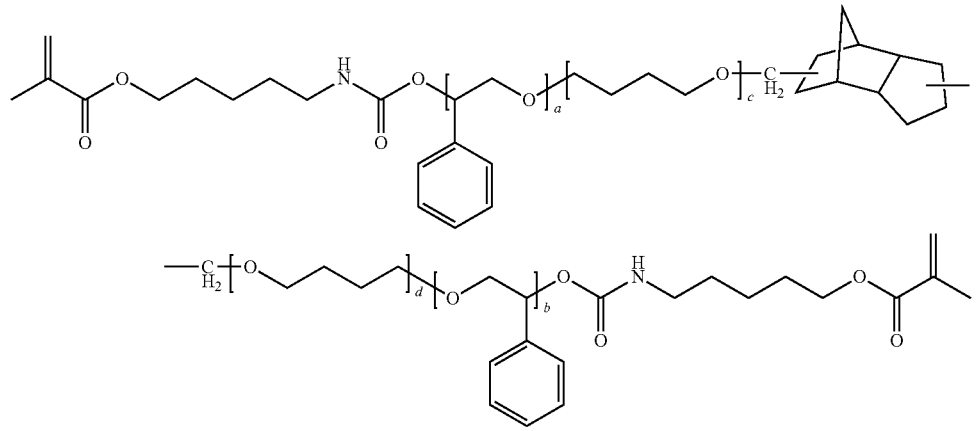

with (a + b) = 1 and (c + d) = 1,
Mw = 783.1

The linking groups of the isocyanurate and tricyclodecane monomers are typically sufficiently low in molecular weight such that the monomer is a stable liquid at 25° C. However, the linking group(s) is typically higher in molecular weight than the oxygen atom of for example 2,2-bis[4-(2-hydroxy-3-methacryloyloxypropoxy)phenyl]propane ("BisGMA"), a common monomer utilized in dental compositions, that links the (meth)acrylate group to the aromatic ring. The molecular weight of the linking group(s) of the monomers described is typically at least 50 g/mole or 100 g/mole. In some embodiments, the molecular weight of the linking group is at least 150 g/mole. The molecular weight of the linking group is typically no greater than about 500 g/mole. In some embodiments, the molecular weight of the linking group is no greater than 400 g/mole or 300 g/mole.

The (i.e. calculated) molecular weight of the isocyanurate and tricyclodecane monomers is typically no greater than 2000 g/mole. In some embodiments, the molecular weight of the monomers is no greater than about 1500 g/mole or 1200 g/mole or 1000 g/mole. The molecular weight of the monomers is typically at least 600 g/mole.

Increasing the molecular weight without forming a solid at 25° C. can be achieved by various synthetic approaches, as depicted above. In some embodiments, the linking groups have one or more pendant substituents. For example, the linking groups may comprise one or more hydroxyl group substituents such an in the case of linking groups comprising alkoxy segments. In other embodiments, the linking groups are branched, and/or comprise at least one (i.e. aliphatic) cyclic moiety, and/or comprise at least one aromatic moiety.

In some embodiments, a by-product is formed during the synthesis of the monomer that may be a solid at about 25° C. (i.e. +/−2° C.). Such by-product is typically removed from the liquid monomer. Hence, the liquid monomer is substantially free of such solid fractions. However, it is contemplated that the liquid monomer may further comprise (e.g. non-crystalline) solid reaction by-products that are soluble in the liquid monomer.

The liquid isocyanurate and tricyclodecane monomers are (e.g. highly) viscous liquids at about 25° C., yet are flowable. The viscosity as can be measured with a Haake RotoVisco RV1 device, as described in EP Application No. 10168240.9, filed Jul. 2, 2010 is typically at least 300, or 400, or 500 Pa*s and no greater than 10,000 Pa*s. In some embodiments, the viscosity is no greater than 5000 or 2500 Pa*s.

In favored embodiments, the isocyanurate and tricyclodecane monomers described herein are stable liquids at about 25° C. meaning that the monomer do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

The isocyanurate and tricyclodecane monomers generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

The compositions described herein advantageously have been found to have a low volume shrinkage. Preferred (e.g. filled) dental compositions (useful for restorations such as fillings and crowns) described herein typically exhibit a Watts Shrinkage of less than about 2%. In some embodiments, the Watts Shrinkage is not greater than 1.95%, or no greater than 1.90%, or no greater than 1.85%, or no greater than 1.80%. In favored embodiments, the Watts Shrinkage is no greater than 1.75%, or no greater than 1.70%, or no greater than 1.65%, or no greater than 1.60%, or no greater than 1.55%, or no greater than 1.50%, or no greater than 1.45%, or no greater than 1.40%, or no greater than 1.35%, or no greater than 1.30%.

The compositions described herein advantageously have been found to exhibit low stress deflection, as measured according to the test method described in the examples. Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). Preferred (e.g. filled) dental compositions (useful for restorations such as fillings and crowns) described herein typically exhibit a stress deflection of no greater than 2.5, or 2.0, or 1.8, or 1.6, or 1.4 microns.

Although the (unfilled) polymerizable resin portion may comprise solely one or more multifunctional ethylenically unsaturated isocyanurate monomer(s) in combination with one or more multifunctional ethylenically unsaturated tricyclodecane monomer, in some embodiments, the (unfilled) polymerizable resin portion comprises a small concentration of other monomer(s). By "other" is it meant an ethylenically unsaturated monomer such as a (meth)acrylate monomer that is not a multifunctional ethylenically unsaturated isocyanurate monomer or a multifunctional ethylenically unsaturated tricyclodecane monomer.

The concentration of such other monomer(s) is typically no greater than 20 wt-%, 19 wt-%, 18 wt-%, 17 wt-%, 16 wt-%, or 15 wt-% of the (unfilled) polymerizable resin portion. The concentration of such other monomers is typically no greater than 5 wt-%, 4 wt-%, 3 wt-%, or 2 wt-% of the filled polymerizable dental composition.

In some embodiments, the dental composition comprises a low viscosity reactive (i.e. polymerizable) diluent. Reactive diluents typically have a viscosity as can be measured with a Haake RotoVisco RV1 device, as described in EP Application No. 10168240.9, filed Jul. 2, 2010 of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono (meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent
comprises one or two spacer unit(s) (S) being connected to the backbone unit (U) via an ether linkage; such as described in EP Application No. 10168240.9, filed Jul. 2, 2010; incorporated herein by reference. One illustrative tricyclodecane reactive diluent has the general structure:

The (e.g. dental) composition may optionally comprises other ethylenically unsaturated (e.g. (meth)acrylate) monomers having a low volume shrinkage (i.e. a monomer that exhibits a Watts Shrinkage Other low volume shrinkage monomers include polymerizable compounds having at least one cyclic allylic sulfide moiety such as described in US2008/0194722; methylene dithiepane silanes as described in U.S. Pat. No. 6,794,520; oxetane silanes such as described in U.S. Pat. No. 6,284,898; and di-, tri, and/or tert-(meth)acryloyl-containing materials such as described in WO2008/082881; each of which are incorporated herein by reference.

US2008/0194722 describes a polymerizable compound having at least one cyclic allylic sulfide moiety with at least one (meth)acryloyl moiety.

Such a polymerizable compound is referred to herein as a hybrid monomer or a hybrid compound. The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth) acrylate moiety) or a (meth)acryloylamino (i.e., a (meth) acrylamide moiety).

In one embodiment, the other low shrinkage monomer includes those represented by the formulae:

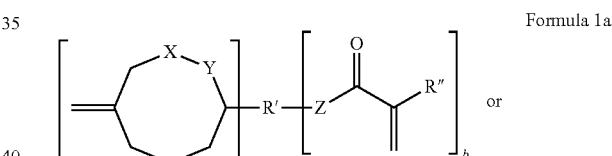

Formula 1a

Formula 1b

In the above formulae, each X can be independently selected from S, O, N, C (e.g., $CH_2$ or CRR, where each R is independently a H or an organic group), SO, $SO_2$, N-alkyl, N-acyl, NH, N-aryl, carboxyl or carbonyl group, provided that at least one X is S or a group comprising S. Preferably, each X is S.

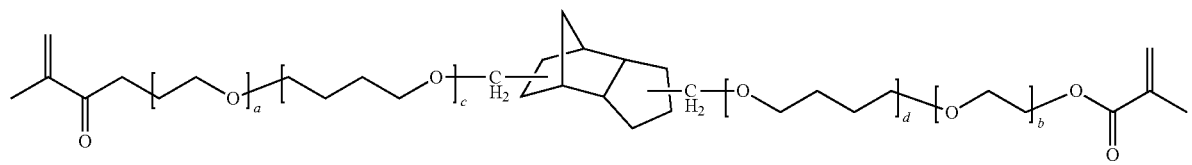

(a + b) = 1 and (c + d) = 1,
Mw = 448.6; $n_D^{20}$ = 1.499; η = 0.1 Pa*s.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

Z is O, NH, N-alkyl (straight chain or branched), or N-aryl (phenyl or substituted phenyl).

The R' group represents a linker selected from alkylene (typically having more than one carbon atom, i.e. excluding methylene), alkylene optionally including a heteroatom (e.g., O, N, S, S—S, SO, $SO_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, alkylthio, carbonyl, acyl, acyloxy, amido, urethane group, urea group, a cyclic allylic sulfide moiety, or combinations thereof.

R" is selected from H, and $CH_3$, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, alkylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

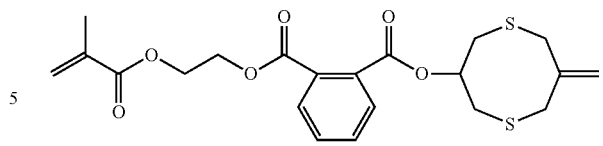

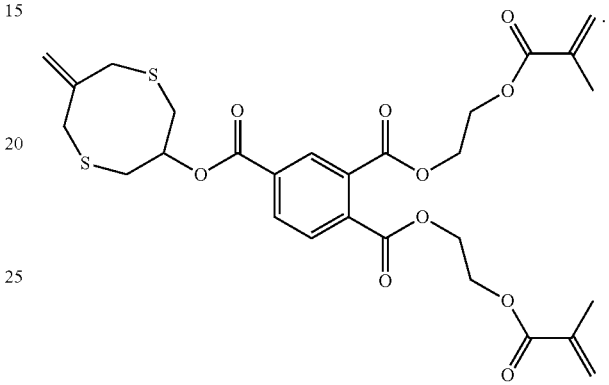

The inclusion of a polymerizable compound having at least one cyclic allylic sulfide moiety can result in a synergistic combination of low volume shrinkage in combination with high diametral tensile strength.

Other suitable low shrink monomers are described in US2008/0194722.

Another low shrinkage monomer includes at least one di-, tri-, and/or tetra(meth)acryloyl-containing materials having the general formula:

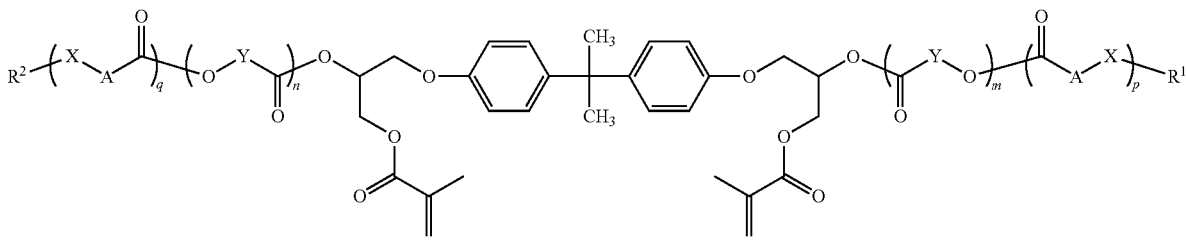

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

Representative polymerizable compounds having at least one cyclic allylic sulfide moiety with at least one (meth) acryloyl moiety include the following wherein: each X independently represents an oxygen atom (O) or a nitrogen atom (N); Y and A each independently represent an organic group, and $R^1$ represents —C(O)C($CH_3$)=$CH_2$, and/or (ii) q=0 and $R^2$ represents —C(O)C($CH_3$)=$CH_2$; m=1 to 5; n=0 to 5; p and q are independently 0 or 1; and $R^1$ and $R^2$ each independently represent H, —C(O)CH=$CH_2$, or —C(O)C($CH_3$)=$CH_2$. In some embodiments, Y does not represent —$NHCH_2CH_2$— when p=0.

The other monomer can be a conventional hardenable (meth)acrylate monomers, such as ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), and polyethyleneglycol dimethacrylate (PEGDMMA). In one embodiment, the combination of polymerizable isocyanurate liquid monomer and tricyclodecane monomer is used in place of (meth)acrylate monomers formed from bisphenol A and thus the dental composition is free of (meth)acrylate monomers formed from bisphenol A.

The curable component of the curable dental composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl (meth)acrylate, ethyl (meth)acrylate, isopropyl(meth)acrylate, n-hexyl(meth)acrylate, stearyl (meth)acrylate, allyl(meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups in a single molecule. Examples of such materials include hydroxyalkyl(meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are available from a wide variety of commercial sources, such as Sigma-Aldrich, St. Louis.

The dental compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate (e.g., HEMA) phosphates, bis((meth)acryloxyethyl) phosphate, ((meth)acryloxypropyl)phosphate, bis((meth)acryloxypropyl)phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler.

The curable dental compositions can include at least 1 wt-%, at least 3 wt-%, or at least 5 wt-% ethylenically unsaturated compounds with acid functionality, based on the total weight of the unfilled composition. The compositions can include at most 80 wt-%, at most 70 wt-%, or at most 60 wt-% ethylenically unsaturated compounds with acid functionality.

The curable dental compositions may include resin-modified glass ionomers cements such as those described in U.S. Pat. No. 5,130,347 (Mitra) U.S. Pat. No. 5,154,762 (Mitra) U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the mixture of monomers is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)bu-tanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azobisisobutyronitrile, as well as dicumyl peroxide, which is favored for mill blanks.

In some embodiments, such as when the dental composition is employed as a dental restorative (e.g. dental filling or crown) or an orthodontic cement, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

The (e.g. filled) dental composite materials typically exhibit a diametral tensile strength (DTS) of at least about 70, 75, or 80 MPa and/or a Barcol Hardness of at least about 60, or 65, or 70-. The depth of cure ranges from about 4 to about 5 and comparable to commercially available (e.g. filled) dental compositions suitable for restorations.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387, 981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503, 169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs.

The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1 wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface. The dental article may comprise a cured composition comprising a polymerizable isocyanurate and tricyclodecane liquid monomer as described herein.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

Test Methods

Stress Test Method

Figure 2:
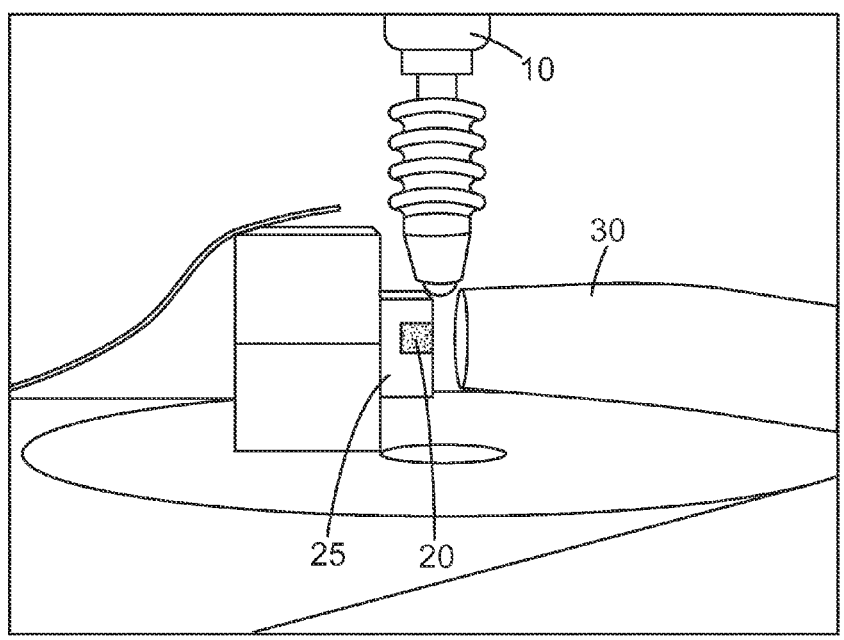
FIG. 2 depicts a Stress Deflection testing apparatus.

To measure stress development during the curing process, a sample holder 25 for the dental composition was prepared by machining a slot into a rectangular 15×8×8 mm aluminum block, as shown in FIG. 1. The slot was 8 mm long, 2.5 mm deep, and 2 mm across, and was located 2 mm from an edge, thus forming a 2 mm wide aluminum cusp adjacent to a 2 mm wide cavity. Prior to testing, the slot in the aluminum block was sandblasted using Rocatec Plus Special Surface Coating Blasting Material (3M ESPE), treated with RelyX Ceramic Primer (3M ESPE), and treated with a dental adhesive, Adper Easy Bond (3M ESPE). The sandblasted slot was filled with an (uncured) dental composition to be tested. The slot was fully packed with each of the compositions tested which was approximately 100 mg of material. As shown in FIG. 2, a linear variable displacement transducer 10 (Model GT 1000, RDP Electronics, United Kingdom) was positioned as shown to measure the displacement of the cusp tip as the dental composition 20 photocured at room temperature. The material was irradiated for 1 minute with a dental curing lamp 30 (Elipar S-10, 3M ESPE) positioned almost in contact (<1 mm) with the material in the slot, then the displacement of the cusp in microns was recorded 9 minutes after the lamp was extinguished. Since the dental composition is cured within the sample holder 25 during testing, a new sample holder is used each time.

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. The results are reported as negative % shrinkage.

Diametral Tensile Strength (DTS) Test Method

Diametral tensile strength of a test sample was measured according to the following procedure. An uncured composite sample was injected into a 4-mm (inside diameter) glass tube; the tube was capped with silicone rubber plugs. The tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany) Cured samples were allowed to stand for 1 hour at about 37° C./90%+ Relative Humidity. The sample was cut with a diamond saw to form 2.2-mm thick disks, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Six disks of cured samples were prepared and measured with results reported in MPa as the average of the six measurements.

Barcol Hardness Test Method

Barcol Hardness of a test sample was determined according to the following procedure. An uncured composite sample was cured in a 2.5-mm or 4-mm thick TEFLON mold sandwiched between a sheet of polyester (PET) film and a glass slide for 30 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure.

Depth of Cure Test Method

The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

| Abbreviation | Chemical Description (Supplier, Location) |
|---|---|
| | Polymerizable Monomer |
| HEMA | 2-hydroxyethyl methacrylate, (Sigma Aldrich) |
| DCC | dicyclohexyl carbodimide, (TCI) |
| | Inorganic Filler |
| Zr/Si filler | One hundred parts zirconia silica filler of average particle size 0.6-0.9 micrometers was mixed with deionized water at a solution temperature of between 20-30° C., and the pH is adjusted to 3-3.3 with trifluoroacetic acid (0.278 parts). The A-174 silane was added to the slurry in an amount 7 parts and the blend is mixed over 2 hours. At the end of 2 hours, the pH is neutralized with calcium hydroxide. The filler is dried, crushed and screened through a 74 or 100 micron screen. |
| | Components of Photoinitiator Package |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; (Alpha Aesar, Ward Hill, MA) |
| EDMAB | ethyl 4-(N,N-dimethylamino)benzoate (Sigma-Aldrich) |

Isocyanurate Trimer—Synthesis of Tri-HydroxyEthyl Iso Cyanurate Tris HEMA Phthalate Phthalic acid anhydride (57.0 g, 0.385 mol, CAS #85-33-9, Alfa Aesar, lot G30T004), 4-(dimethylamino)pyridine (DMAP, 4.9 g, 0.04 mol, CAS #1122-58-3, Alfa Aesar, lot L125009), 2-hydroxyethylmethacrylate (HEMA, 50.9 g, 0.391 mol, and butylated hydroxytoluene (BHT, 0.140 g) were charged into a 2-liter 3-neck reaction flask equipped with a mechanical stirrer, a thermocouple connected to a temperature controller, a dry air stream running through a T-shape connection into the reactor then to an oil bubbler, and a heating mantle. With continuous stirring, the flask contents were heated to 95° C., by which all components dissolved and a clear liquid was obtained. Heating at 95° C. and stirring were continued for 5 hours. The heat was turned off and the flask contents were allowed to cool to room temperature while still being stirred under dry air. Acetone (250 ml) was added followed by tris-(2-hydroxyethyl)isocyanurate (33.58 g, 0.158 mol, from TCI America, Portland, Oreg.). The heating mantle was replaced with an ice bath, where the mixture was cooled to 0-5° C. A solution made from dicyclohexyl carbodiimide (DCC, 81 g, 0.393 mol) in 120 ml acetone was placed into a 500 ml dropping funnel which was placed in-between the reaction flask and the dry air in-let. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate:hexanes, 2:1 by volume. The obtained solution was extracted with 200 ml of 1.0 N. HCl, 200 ml of 10% aqueous, 200 ml H$_2$O, and 200 ml brine. The organic layer was concentrated in a rotary evaporator with 40° C. bath. Further drying was done under a vacuum pump at 50° C. for 3 hours with air bleeding into the product during the whole time to give an almost colorless hazy viscous liquid.

Refractive index was measured and found to be 1.5386. By use of NMR the liquid was determined to be the product shown is the following reaction scheme. The calculated molecular weight of the depicted end product was determined to be 1041 g/mole.

The calculated molecular weight of the linking group was determined to be 220 g/mole.

Synthesis of TGP-IEM

General Procedure 1: Reaction of a Diol-Precursor with Epoxy Components Using TEAA as Catalyst E.g. TCD alcohol and GMA as the corresponding epoxy functional reagent/s are mixed while stirring with e.g. cyclohexane. 1.5 wt.-% of TEA and 1.5 wt.-% of GAA (with respect to the mass of the sum of all reactants, to form in situ TEAA), 1000 ppm of HQ, 200 ppm of BHT, and 200 ppm of HQME are added while stirring. Then the mixture is heated while stirring a temperature of about 70° C. until completion of the addition reaction (measured via $^1$H-NMR: no signals of residual epoxy groups were detected). Optionally, 3 to 5 wt.-% of MSA is slowly added while stirring and stirring is continued for about 60 min at about 70° C. Then the mixture is allowed to cool to room temperature while stirring. The

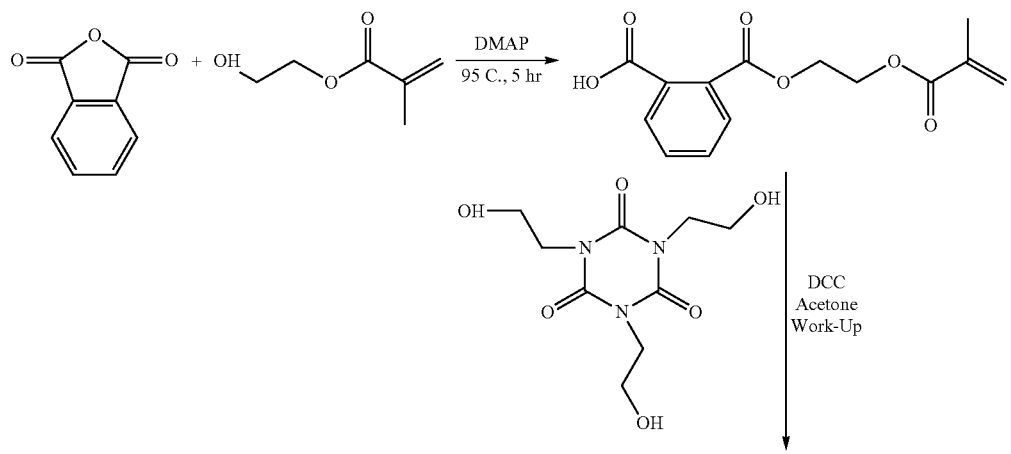

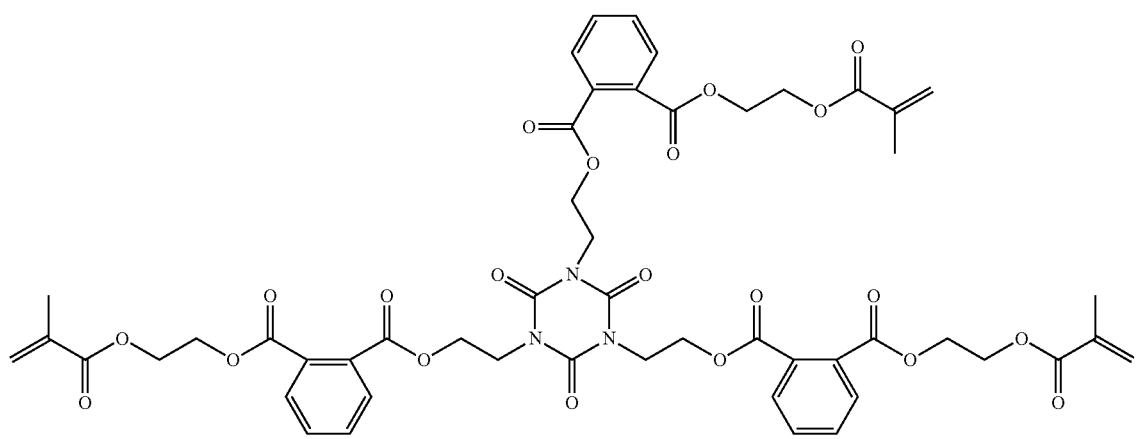

upper cyclohexane phase is separated from the oily viscous lower phase if existent. The separated cyclohexane phase is washed once with water, then extracted twice with 2N NaOH solution, then once washed with water, then dried over anhydrous $Na_2SO_4$. After filtration, the filtrate is again filtered through basic alumina. 100 ppm of BHT and 100 ppm of HQME are added to the filtrate. Then the solvent is stripped off in vacuum while air is bubbling through the crude sample.

According to General Procedure 1 100 g of TCD alcohol, 155 g of GP, and 3.00 g of MSA were reacted. 253 g of TGP (509 mmol, 99%) were isolated as yellow oil. According to General Procedure 4 100 g of TGP and 59.4 g of IEM were reacted. 158 g of TGP-IEM (196 mmol, 99%) were isolated as yellow oil: $\eta=1400$ Pa*s, $n_D^{20}=1.531$.

Synthesis of TTEO-IEM

General Procedure 2: Reaction of a Diol-Precursor Like with Epoxy Components Containing Mixtures (e.g. EO in THF) Using $BF_3$*THF as Catalyst E.g. TCD alcohol is diluted in anhydrous THF, then $BF_3$*THF is added while stirring. Gaseous EO is added while stirring so that the temperature of the reaction mixture does not exceed about 30-40° C. After completion of the EO addition stirring is continued at room temperature for about 30 min. 13 wt.-% of water (with respect to the sum of the amounts of the reactive educts) are added, after about 30 min while stirring 13 wt.-% of basic alumina is added, too. After additional about 60 min of stirring 13 wt.-% of a solution of sodium methanolate in methanol (30% in methanol) is added. Then the suspension is stirred at room temperature for about 12 h. After filtration the solvent is stripped off in vacuum.

According to General Procedure 2 300 g of TCD alcohol, 64.6 g of EO, 600 g of THF, and 37.9 g of $BF_3$*THF were reacted. 429 g of TTEO were isolated as colorless oil. According to General Procedure 4 55.3 g of TTEO and 54.7 g of IEM were reacted. 100 g of TTEO-IEM (95%) were isolated as colorless oil: $\eta=45$ Pa*s, $n_D^{20}=1.503$.

Synthesis of TTEO-MA

General Procedure 3: Reaction of a Diol-Precursor Like e.g. TCD Alcohol with Epoxy Containing Mixtures (e.g. EO in THF) Using $BF_3$*THF as Catalyst E.g. TCD alcohol is diluted in anhydrous THF, then $BF_3$*THF is added while stirring. Gaseous EO is added while stirring so that the temperature of the reaction mixture does not exceed about 30-40° C. After completion of the EO addition stirring is continued at room temperature for about 30 min. 13 wt.-% of water (with respect to the sum of the amounts of the reactive educts) are added, after about 30 min while stirring 13 wt.-% of basic alumina is added, too. After additional about 60 min of stirring 13 wt.-% of a solution of sodium methanolate in methanol (30% in methanol) is added. Then the suspension is stirred at room temperature for about 12 h. After filtration the solvent is stripped off in vacuum.

According to General Procedure 3 300 g of TCD alcohol, 64.6 g of EO, 600 g of THF, and 37.9 g of $BF_3$*THF were reacted. 429 g of TTEO were isolated as colorless oil. According to General Procedure 4 213 g of TTEO, 161 g of MA, 44.8 mg of BHT, 121 mg of HQME, 89.6 mg of methylene blue, and 12.8 g of MSA were reacted using hexane as solvent. 237 g of TTEO-MA (67%) were isolated as colorless liquid: $\eta=0.1$ Pa*s, $n_D^{20}=1.499$.

The wt.-% of the following components, as described in the following table, were combined to form polymerizable restorative materials.

|  | TTEO-IEM | TGP-IEM | Isocyanurate Trimer | TTEO-MA | CPQ | EDMAB | DPIHFP | Zr/Si Filler |
|---|---|---|---|---|---|---|---|---|
| Ex. 1 | 9.599 |  | 9.655 | 1.951 | 0.037 | 0.209 | 0.108 | 78.44 |
| Ex. 2 | 9.995 |  | 10.162 | 1.055 | 0.032 | 0.216 | 0.11 | 78.43 |
| Ex. 3 | 9.925 |  | 10.063 | 1.039 | 0.032 | 0.181 | 0.092 | 78.67 |
| Ex. 4 | 9.907 |  | 10.043 | 1.055 | 0.036 | 0.209 | 0.109 | 78.64 |
| Ex. 5 |  | 9.599 | 9.655 | 1.951 | 0.037 | 0.209 | 0.108 | 78.44 |

The compositions were tested according to the previously described test methods. The results were as follows:

|  | Stress, um deflection (std. dev., n = 3) | Watts shrinkage, negative % (std. dev., n = 5) | Diametral tensile strength, MPa (std. dev., n = 6) | Barcol hardness, 2.5 mm, top (std. dev., n = 6) | Barcol hardness, 2.5 mm, bottom (std. dev., n = 6) | Barcol hardness, 4.0 mm, top (std. dev., n = 6) | Barcol hardness, 4.0 mm, bottom (std. dev., n = 6) | Depth of Cure, mm (std. dev., n = 3) |
|---|---|---|---|---|---|---|---|---|
| Ex. 1 | 2.01 (0.11) | 1.51 (0.04) | 87.8 (5.2) | 67.5 (2.5) | 65.7 (2.1) | 67.7 (2.6) | 72.8 (1.6) | 5.04 (0.11) |
| Ex. 2 | 2.02 (0.13) | 1.42 (0.04) | 88.3 (2.1) | 71.8 (0.8) | 66.5 (1.8) | 71.0 (1.1) | 68.5 (0.8) | 5.08 (0.03) |
| Ex. 3 | 1.78 (0.16) | 1.39 (0.03) | 87.9 (12.7) | 66.7 (1.8) | 71.0 (1.6) | 69.5 (1.9) | 70.7 (1.2) | 4.55 (0.14) |
| Ex. 4 | 1.71 (0.06) | 1.36 (0.02) | 76.9 (3.8) | 64.2 (0.8) | 69.7 (2.4) | 65.3 (1.2) | 70.0 (1.3) | 4.38 (0.06) |
| Ex. 5 | 1.35 (0.17) | 1.28 (0.05) | 78.5 (3.2) | 65.3 (0.8) | 69.5 (2.3) | 66.5 (3.4) | 61.3 (3.7) | 4.70 (0.05) |

What is claimed is:

1. A hardenable dental composition comprising
at least one isocyanurate monomer comprising at least two ethylenically unsaturated groups bonded to nitrogen atoms of a trivalent isocyanuric acid ring via a divalent linking group comprising a cyclic or aromatic moiety;
at least one multifunctional ethylenically unsaturated tricyclodecane monomer, and inorganic nanoparticles comprising silica, zirconia, or mixtures thereof.

2. The hardenable dental composition of claim 1 wherein the isocyanurate monomer and tricyclodecane monomer are liquids at 25° C.

3. The hardenable dental composition of claim 1 wherein the ethylenically unsaturated groups of the monomers are (meth)acrylate groups.

4. The hardenable dental composition of claim 1 wherein the isocyanurate and tricyclodecane monomers have a refractive index of at least 1.50.

5. The hardenable dental composition of claim 1 wherein the isocyanurate and tricyclodecane monomers have a molecular weight (Mw) ranging from about 600 to 1500 g/mole.

6. The hardenable dental composition of claim 1 wherein the isocyanurate monomer has the general structure

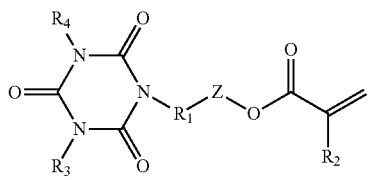

wherein
$R_1$ is alkylene, arylene, or alkarylene, optionally including a heteroatom;
$R_2$ is hydrogen or methyl;
Z is an alkylene, arylene, or alkarylene linking group comprising one or more moieties selected from urethane, ester, thioester, ether, thioether, and at least one Z comprises a cyclic or aromatic moiety; and
at least one of $R_3$ or $R_4$ is

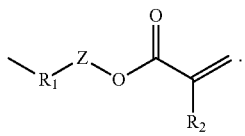

7. The hardenable dental composition of claim 6 wherein the isocyanurate monomer is a di(meth)acrylate isocyanurate monomer.

8. The hardenable dental composition of claim 6 wherein the isocyanurate monomer is a tri(meth)acrylate isocyanurate monomer.

9. The hardenable dental composition of claim 6 wherein Z comprises at least one ester moiety.

10. The hardenable dental composition of claim 1 wherein the multifunctional ethylenically unsaturated tricyclodecane monomer has a backbone unit (U) having the structure

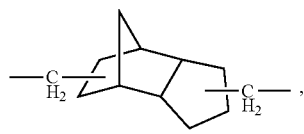

wherein one or two spacer unit(s) (S) are bonded to the backbone unit (U) via an ether linkage and at least one spacer unit (S) comprises a CH(Q)-OG chain wherein each group G comprising a (meth)acrylate moiety and Q comprises at least one group selected from hydrogen, alkyl, aryl, alkaryl and combinations thereof.

11. The hardenable dental composition of claim 10 wherein G is bonded to the spacer unit(s) (S) via a urethane moiety.

12. The hardenable dental composition according to claim 10 wherein the spacer unit(s) (S) comprises a moiety being selected from

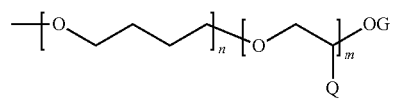

wherein m is 1 to 3; n is 1 to 3; and Q is hydrogen, methyl, phenyl, phenoxymethyl; or

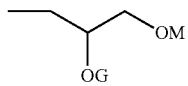

wherein M is phenyl.

13. The hardenable dental composition according to claim 10, wherein the tricyclodecane monomer is characterized by a structure according to formulas

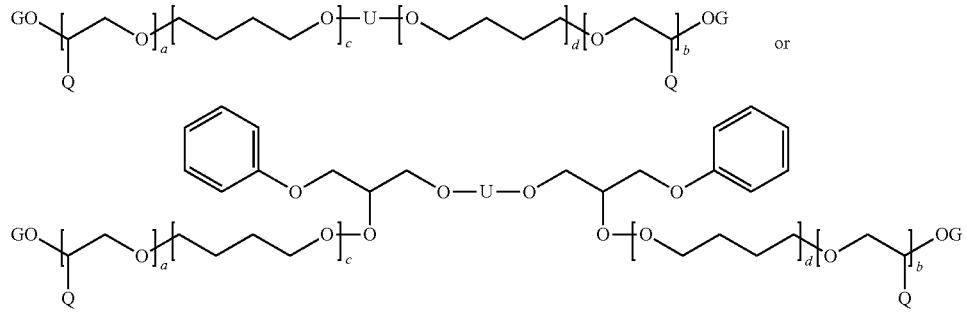

wherein a, b is 0 to 3; c, d is 0 to 3; (a+b) is 1 to 6, (c+d) is 1 to 6; and Q is independently selected from hydrogen, methyl, phenyl or phenoxymethyl.

14. The hardenable dental composition of claim 1 wherein the inorganic nanoparticles are in the form of nanoclusters.

15. The hardenable dental composition of claim 1 wherein the dental composition further comprises other (meth)acrylate monomers.

16. The hardenable dental composition of claim 15 wherein the other monomer comprises an isocyanurate or tricyclodecane monomer having a molecular weight no greater than 600 g/mole.

17. The hardenable dental composition of claim 1 wherein the hardened composition exhibits a Watts Shrinkage of less than about 2%.

18. The hardenable dental composition of claim 1 wherein the hardened composition exhibits a Diametral Tensile Strength is at least 75 MPa.

19. The hardenable dental composition of claim 1 wherein the hardened composition exhibits a stress deflection no greater than 2.0 microns.

20. A method of treating a tooth surface, the method comprising
providing a hardenable dental composition according to claim 1,
placing the dental composition on a tooth surface in the mouth of a subject; and
hardening the hardenable dental composition.

21. A dental article comprising a hardenable dental composition according to claim 1, wherein the hardenable dental composition is at least partially hardened.

22. A method of treating a tooth surface, the method comprising
providing an at least partially hardened dental article according to claim 21,
adhering the dental article on a tooth surface in the mouth of a subject.

23. The hardenable dental composition of claim 1 wherein the hardened composition exhibits a stress deflection no greater than 1.6 microns.

* * * * *

UNITED STATES PATENT AND TRADEMARK OFFICE
CERTIFICATE OF CORRECTION

| | |
|---|---|
| PATENT NO. | : 9,012,531 B2 |
| APPLICATION NO. | : 13/995858 |
| DATED | : April 21, 2015 |
| INVENTOR(S) | : Abuelyaman et al. |

Page 1 of 1

It is certified that error appears in the above-identified patent and that said Letters Patent is hereby corrected as shown below:

In the Specification

Column 3
Line 37, Delete "iscosyanurate" and insert -- isocyanurate --, therefor.

Column 5
Line 26, Delete "methaycrylated" and insert -- methacrylated --, therefor.

Column 11
Line 48, Delete "herein" and insert -- herein. --, therefor.

Column 26
Line 66, Delete "triethlyene" and insert -- triethylene --, therefor.

Column 27
Line 1, Delete "ethylenegylcol" and insert -- ethyleneglycol --, therefor.
Line 35, Delete "bisphenolA" and insert -- bisphenol A --, therefor.

Column 29
Line 17, Delete "tetrafluoroboarate." and insert -- tetrafluoroborate. --, therefor.

Column 38
Line 17, Delete "carbodimide," and insert -- carbodiimide, --, therefor.

Signed and Sealed this
Tenth Day of November, 2015

Michelle K. Lee
*Director of the United States Patent and Trademark Office*